(12) United States Patent
de Boer et al.

(10) Patent No.: US 10,561,809 B2
(45) Date of Patent: Feb. 18, 2020

(54) BREATH ACTUATED DRY POWDER INHALER

(71) Applicant: Rijksuniversiteit Groningen, Groningen (NL)

(72) Inventors: Anne Haaije de Boer, Groningen (NL); Paul Hagedoorn, Groningen (NL); Henderik Willem Frijlink, Groningen (NL)

(73) Assignee: Rijksuniversiteit Groningen, Groningen (NL)

( * ) Notice: Subject to any disclaimer, the term of this patent is extended or adjusted under 35 U.S.C. 154(b) by 524 days.

(21) Appl. No.: 15/316,134

(22) PCT Filed: Jun. 5, 2015

(86) PCT No.: PCT/NL2015/050413
§ 371 (c)(1),
(2) Date: Dec. 2, 2016

(87) PCT Pub. No.: WO2015/187205
PCT Pub. Date: Dec. 10, 2015

(65) Prior Publication Data
US 2017/0113008 A1    Apr. 27, 2017

(30) Foreign Application Priority Data
Jun. 6, 2014    (EP) ..................................... 14171551

(51) Int. Cl.
*A61M 15/00*    (2006.01)

(52) U.S. Cl.
CPC .... *A61M 15/0086* (2013.01); *A61M 15/0021* (2014.02); *A61M 15/0091* (2013.01); *A61M 2202/064* (2013.01); *A61M 2206/16* (2013.01)

(58) Field of Classification Search
CPC .............. A61M 15/00; A61M 15/0001; A61M 15/0006; A61M 15/0008; A61M 15/002;
(Continued)

(56) References Cited

U.S. PATENT DOCUMENTS

| | | | | |
|---|---|---|---|---|
| 4,446,862 A | * | 5/1984 | Baum | A61M 15/0028 128/203.15 |
| 5,301,666 A | * | 4/1994 | Lerk | A61M 15/002 128/203.15 |

(Continued)

FOREIGN PATENT DOCUMENTS

| | | | | |
|---|---|---|---|---|
| EP | 1488819 A1 | * | 12/2004 | ........ A61M 15/0045 |
| EP | 1488819 A1 | | 12/2004 | |

OTHER PUBLICATIONS

International Search Report and Written Opinion dated Jul. 22, 2015, from International Application No. PCT/NL2015/050413 (9 pages).

*Primary Examiner* — Timothy A Stanis
*Assistant Examiner* — Matthew D Ziegler
(74) *Attorney, Agent, or Firm* — Kilpatrick Townsend & Stockton LLP

(57) ABSTRACT

A breath actuated dry powder inhaler with a single air circulation chamber for de-agglomeration of entrained powdered medicament using the energy of the inspiratory air stream. The chamber has a substantially polygonal sidewall, a plurality of air supply channels entering the chamber substantially tangentially to its sidewall. A powder channel extends through a powder dose supply region of the inhaler tangentially into the chamber. An air outlet axially extends from a discharge and connects to a discharge channel that extends to a mouthpiece. The polygonal sidewall comprises at least six straight line segments, each straight line segments being spaced at the same first distance from an adjacent one forming the plurality of air supply channels.

(Continued)

Figure 1:
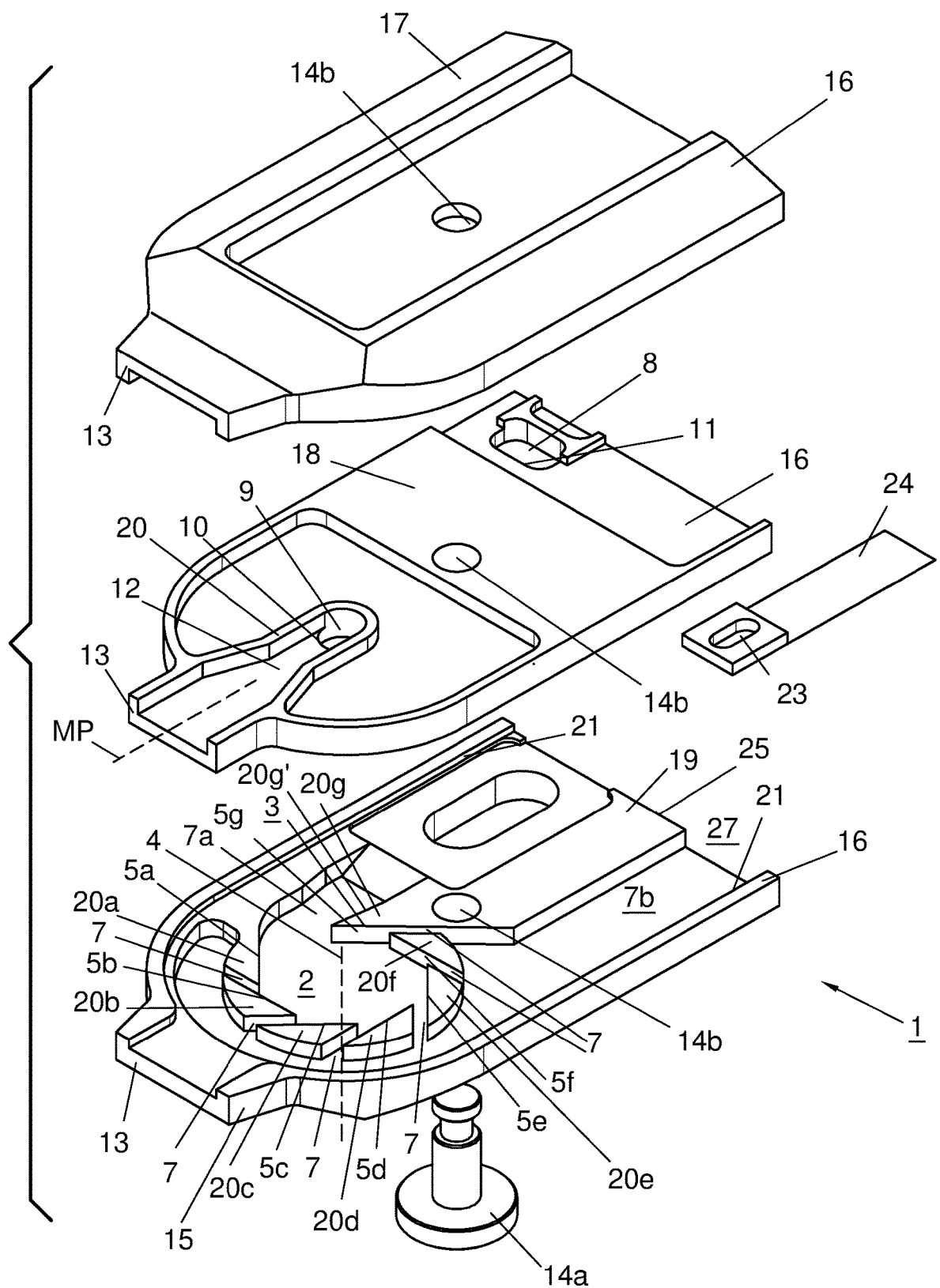

The air supply channels have the same width. The powder channel is defined by two straight line segments which are spaced from each other at a second distance which is larger than the first distance.

9 Claims, 3 Drawing Sheets

(58) Field of Classification Search
CPC .......... A61M 15/0021; A61M 15/0028; A61M 15/003; A61M 15/0043; A61M 15/0045; A61M 15/0046; A61M 15/0061; A61M 15/0063; A61M 15/0086; A61M 15/0091; A61M 2202/064; A61M 2206/10; A61M 2206/12; A61M 2206/16; A61M 2210/06; A61M 2210/0625; A61M 11/001; A61M 11/003
See application file for complete search history.

(56) References Cited

U.S. PATENT DOCUMENTS

| | | | |
|---|---|---|---|
| 5,840,279 A | 11/1998 | Narodylo et al. | |
| 6,026,808 A * | 2/2000 | Armer | A61M 15/0086 128/200.23 |
| 6,257,231 B1 * | 7/2001 | Shick | A61M 15/0086 128/200.14 |
| 6,347,629 B1 | 2/2002 | Braithwaite | |
| 6,367,471 B1 * | 4/2002 | Genosar | A61M 15/0086 128/200.23 |
| 6,418,926 B1 * | 7/2002 | Chawla | A61J 1/00 128/203.12 |
| 8,550,074 B2 * | 10/2013 | Jones | A61M 15/0028 128/203.21 |
| 8,714,149 B2 * | 5/2014 | Blair | A61M 15/0065 128/203.15 |
| 9,283,336 B2 * | 3/2016 | Jones | A61M 15/0028 |
| 2001/0027790 A1 * | 10/2001 | Gieschen | A61M 15/0086 128/203.15 |
| 2002/0033173 A1 * | 3/2002 | Shofner, II | A61M 15/0065 128/200.22 |
| 2003/0015195 A1 | 1/2003 | de Boer et al. | |
| 2004/0107963 A1 * | 6/2004 | Finlay | A61M 15/0086 128/203.15 |
| 2004/0206350 A1 * | 10/2004 | Alston | A61M 15/0028 128/203.12 |
| 2011/0056488 A1 * | 3/2011 | Harmer | A61M 15/0028 128/200.23 |
| 2013/0213397 A1 * | 8/2013 | Curtis | A61M 15/0045 128/203.15 |
| 2014/0137865 A1 * | 5/2014 | Seeney | A61M 15/0043 128/203.15 |

* cited by examiner

BREATH ACTUATED DRY POWDER INHALER

CROSS-REFERENCES TO RELATED APPLICATIONS

This application is a National Stage of International Application No. PCT/NL2015/050413, filed Jun. 5, 2015, and which claims the benefit of European Patent Application No. 14171551.6, filed Jun. 6, 2014, the disclosures of which are incorporated herein by reference.

The invention relates to a breath actuated dry powder inhaler, wherein high doses of a powdered medicament are de-agglomerated in an air circulation chamber using the energy of the inspiratory air stream.

Such a breath actuated dry powder inhaler is known from EP-A1-1,488,819 and is used to deliver drugs to or via the respiratory tract. Such pulmonary drug delivery is not only advantageous in treatment of disorders of the lungs, but is also advantageous for many other types of treatment that conventionally includes oral or parenteral administration of medicine.

Advantages of drug delivery via the pulmonary route over the oral route include rapid delivery to the site of action, higher local concentrations at reduced dose and the possibility to administer relatively large molecules, in particular molecules that exhibit poor or no bioavailability when administered through the oral route.

Advantages of drug delivery via the pulmonary route over the parenteral route include higher ease and better acceptance of the administration and increased patient adherence to the therapy.

De-agglomeration of the inhalation powder in the air circulation chamber or "classifier" chamber is effectuated using the energy of the inspiratory air stream and is necessary to reduce agglomerates and lumps of the unprocessed cohesive powder into a particle size that allows effective penetration and deposition in the target area, e.g. a size smaller than 5 µm, preferably a size within the range from 1 to 3 µm.

Although highly efficient for most powdered medicaments, it appears that specific powdered medicaments which are extremely hygroscopic, and in particular powdered medicaments which also are highly cohesive and adhesive and/or exhibit a high degree of compaction under pressure and tend to stick to the walls of the classifier chamber of the known inhaler. In addition, it appears that even during storage in closed containers large, soft agglomerates of the powder are formed comprising such highly cohesive powdered medicaments which agglomerates clog the powder channel and make the inhaler hard or impossible to use.

The present invention generally aims to alleviate the disadvantages of the known inhaler when using highly hygroscopic and/or adhesive and cohesive materials with a high compaction propensity, while maintaining its advantages.

Thereto, the invention provides for a breath actuated dry powder inhaler. Particles and agglomerates entering the air circulation chamber from the powder channel circulate by action of a drag force imposed by the air flows entering this chamber through the plurality of air supply channels. They move along the periphery of this chamber by centrifugal forces and collide with the straight line segments as a result of which they break up in smaller fragments and the ratio of drag to centrifugal force increases.

By providing the polygonal sidewall with at least six straight sides it appears that the contact surface area between circulating particles and the wall is reduced such that a reduction of adhesion of powder against the wall parts is obtained. In addition, the collision angle, i.e. the angle between the imaginary extension of the sides, has such a value, i.e. 60° or smaller, that the magnitude of the compaction force is also reduced and a higher residual particle velocity after collision is obtained. The many air flows through the air supply channels furthermore create a continuous air barrier for the smaller particles which, in conjunction with the reduced ratio of the centrifugal to drag force, keeps them away from the cylindrical classifier wall and prevents that they contribute to the adhesion and compaction against the classifier sidewall. Instead, it causes them to circulate at a certain distance from the polygonal sidewall and to collide with each other and to disrupt by internal shear in turbulent regions of air flow. Furthermore, since the powder channel is wider than the air supply channels the risk of clogging of the powder channel is reduced, but the symmetry of the air circulation in the chamber is negatively influenced. By providing at least six straight sides the number of air supply channels is large enough so that the air flowing through the air supply channels into the chamber corrects the asymmetry of the air circulation in the chamber such that powder can be dispensed from the inhaler correctly.

In a preferred embodiment of a breath actuated dry powder inhaler according to the invention the polygonal sidewall comprises eleven straight line segments. In this manner compaction can be reduced optimally while providing more air supply channels for an even further optimised air circulation symmetry in the classifier chamber and a lower retention and better dispersion of the powdered medicament.

In a further embodiment of a breath actuated dry powder inhaler according to the invention the second distance is at least twice, preferably three times the first distance. This means that the width of the powder channel is at least twice, preferably three times the width of the air supply channel to prevent at least largely clogging of the powder channel by large agglomerates. As a result of said proportion the air flow in use is also sufficiently strong to break up the large agglomerates in rare cases of clogging, or in other words to open the passageway for the powder flow again. In particular when the first distance (i.e. the width of the air supply channels) is between 1 and 2 mm, preferably about 1.5 mm, cleaning of the walls of the inhaler can be obtained even in case the powdered medicament does not comprise so called sweeper particles. Such sweeper particles are large and strong crystals or agglomerates which do not break up or fragment upon collision with the classifier wall and are retained in the inhaler. They circulate along the periphery of the classifier chamber during the entire inhalation period and sweep adhering drug particles off the cylindrical classifier wall to minimise inhaler retention. In contrast with carrier particles in adhesive mixtures for inhalation, they are not part of the drug formulation and are filled into the dose compartment separately.

In a still further embodiment of a breath actuated dry powder inhaler according the invention, the a surface of each of the projections forms a respective straight line segment, each surface having a free edge, the free edges of the surfaces of the respective projections being situated on a circle around the central axis. Such a positioning is beneficial for the air circulation in the classifier chamber, thereby aiding in effectively dispensing the powdered medicaments to the user and creating a sufficient drag of air for the smaller particles further preventing collision thereof to the walls.

In an advantageous embodiment of a breath actuated dry powder inhaler according to the invention the diameter of the chamber is between about 20 to about 30 mm, preferably about 25 mm. In this manner a good air circulation is obtained in the classifier chamber as a result of which higher dosages can be used while still preventing sticking of material to the sides of the chamber.

Figure 2:
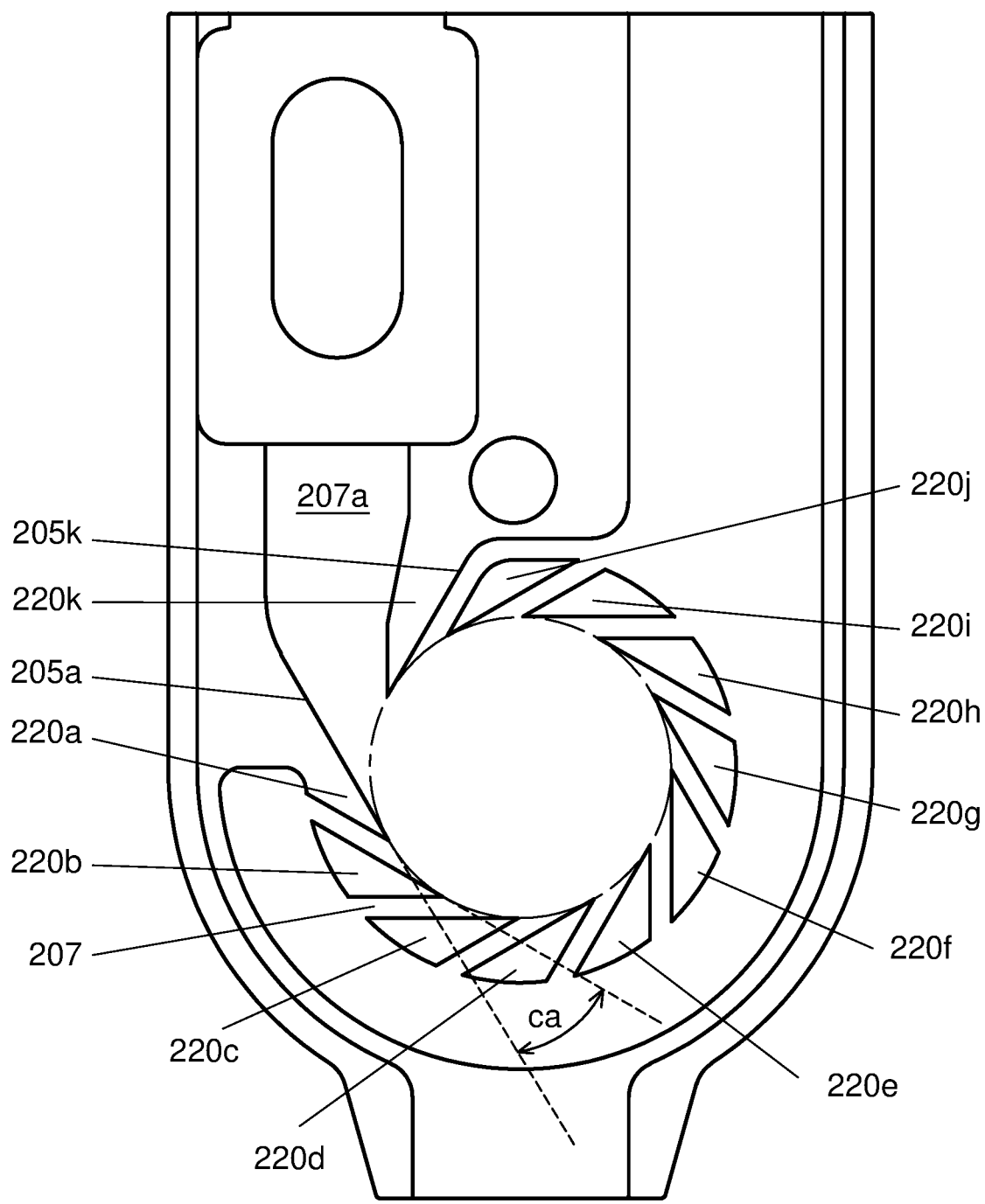
Figure 3:
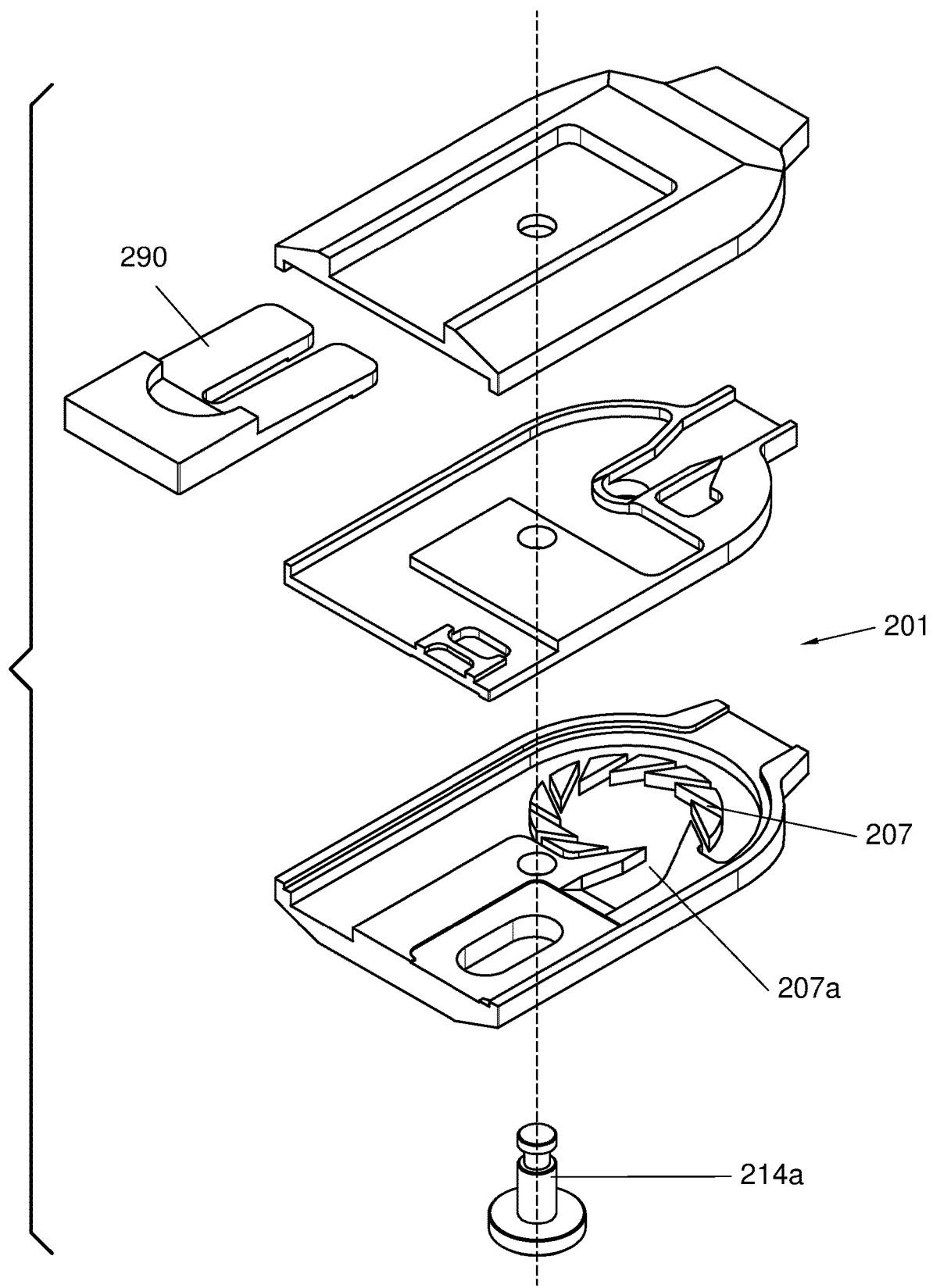

The invention shall be elucidated by way of example only using a number of preferred embodiments shown in a drawing. In the drawing is shown:

FIG. 1 an exploded view of a first embodiment of the breath actuated dry powder inhaler having a single circulation chamber;

FIG. 2 a top plan view of the bottom plate of a second embodiment of an inhaler according to the invention; and FIG. 3 an exploded view of the second embodiment of the breath actuated dry powder inhaler having a single circulation chamber with the bottom plate of FIG. 2.

The drawings show schematical representations of exemplary embodiments, which are given as non-limiting examples of the invention. In the drawing, for the various embodiments, identical or corresponding parts are denoted with the same reference numerals.

FIG. 1 shows a breath actuated dry powder inhaler 1, comprising a single, substantially disc shaped air circulation chamber 2 for de-agglomeration of entrained powdered medicament using the energy of the inspiratory air stream. The chamber 2 has a polygonal sidewall 3 extending about a central axis 4 between a substantially parallel top wall (formed by a substantially planar intermediate plate 18) and bottom wall (formed by a substantially planar bottom plate 19) of the chamber 2 so that the height of the chamber is smaller than its diameter. In the embodiment shown in FIG. 1 the diameter of the single chamber 2 is about 25 mm, but it can in other embodiments have another value between 20 mm and 30 mm. In the embodiment shown in FIG. 1 the polygonal sidewall 3 has seven straight line segments or sides 5*a*-5*g*, being formed by a surface of a respective projection 20. The projections 20*a*-20*b*, 20*b*-20*c*, 20*c*-20*d*, 20*d*-20*e*, 20*e*-20*f* and 20*f*-20*g* are spaced at the same distance (also called first distance) from each other so as to form a plurality of air supply channels 7 (in the embodiment shown in FIG. 1 six) which have the same width and which are regularly disposed about the circumference of the chamber 2, which channels 7 extend from separate air inlets and which channels enter the chamber 2 substantially tangentially to its sidewall 3. Said distance, i.e. the width of the air supply channels, is in the embodiment shown in FIG. 1 about 1.5 mm, but can in other embodiments be between 1 and 2 mm. The projections 20*a* and 20*g*, however, are spaced at a larger distance from each other forming a powder channel 7*a*. In the shown embodiment this larger, second distance (i.e. the width of the powder channel) is about three to four, preferably 3.5 times the first distance, i.e. about 5 mm, but can in other embodiments be at least twice the first distance, i.e. at least 3 mm. The powder channel 7*a* extends from a joint air supply inlet to the powder dose region 8 of the inhaler 1. The chamber 2 further comprises an air outlet 9 axially extending from a discharge opening 10 in the centre of the top wall of the chamber 2 and that connects to a discharge channel 12. The discharge channel 12 extends to a mouthpiece 13. Please note that in FIG. 1 an embodiment is disclosed with seven sides, but that the invention is not limited to this number and any number of sides can be provided as long as there are more than six sides.

The discharge channel 12 connects substantially transversely to the air outlet 9 of the chamber. The axis MP of the mouthpiece 13 is orientated transversely to the central axis 4 of the classifying chamber 2.

By means of an assembling element 14*a* which can be inserted in respective openings 14*b* of the parts of the inhaler 1 the inhaler 1 can be assembled such that it comprises a substantially planar housing having the shape and size of a thick credit card, being constructed as e.g. a disposable unit. Please note, that the invention is not limited to the manner in which the parts are connected to each other and that e.g. a construction with which the parts are clicked together with flexible lips or tapered pins falling in corresponding holes is also possible. The chamber 2 is disposed in the housing such that the central axis 4 of the chamber 2 extends transversely to the bottom plate 19. The discharge channel 12 is disposed in the housing such that it extends in a plane parallel to the bottom plate. The mouthpiece 13 is provided on a peripheral edge 15 of the housing. The discharge channel 12 and the circulation chamber 2 extend in substantially parallel planes. During inhalation, the mouthpiece 13 discharges an aerosol cloud of de-agglomerated powder particles entrained from the air recirculation chamber 2 in a direction parallel to the longitudinal axis of the inhaler housing which coincides with the axis MP, while the axis of the classifying chamber 2 is perpendicular to the longitudinal axis of the inhaler housing 14.

The housing is thus built up of a stack of substantially planar elements 16. These elements 16 include the bottom plate 19, the intermediate plate 18 and a top plate 17. The planar bottom plate 19 is provided with projections 20 and an opening 10, that in the stack form the chamber 2, the air supply channels 7, the air supply region for the powder flow 8 and the discharge channel 12 of the inhaler 1. The top surface of the bottom plate 19 e.g. forms the bottom wall of the chamber 2, and carries the projections 20 that form the sides 5*a*-5*g*. The free edges of the sides can be rounded off pointing towards the centre of the chamber 2 and are substantially positioned on an imaginary circle. The chamber 2 is closed off by the bottom surface of the intermediate plate 18, forming the top wall of the chamber 2. The intermediate plate 18 forms a division between a bottom plane in which the chamber 2 extends and a parallel top plane in which the discharge channel 12 extends. The discharge opening 10 in the intermediate plate 18 forms a passage for air and entrained, de-agglomerated medicine particles exiting the chamber through air outlet 9 extending co-axially with axis 4.

The bottom plate 19 comprises peripheral ridges 21, defining an aperture in which intermediate plate 18 is placed. Top plate 17 is stacked on top intermediate plate 18 and bottom plate 19. The assembly of the plates 16-18 is such that the housing is substantially airtight.

The powder dose supply area 8 is, in the embodiment shown in FIG. 1, formed by a sealed dose compartment 23 containing a pre-measured dose of powdered medicament. Please note that for clarity of drawing the sealed dose compartment is shown upside down with regard to the use position. The dose compartment 23 is included in the powder channel 7*a* and is blocking air passage through the channel 7*a* until removal of the seal 24 of the dose compartment 23. The sealed dose compartment 23 is shown as a blister pocket sealed with a removable cover foil 24. The blister pocket 23 is included in the stack with the cover foil 24 extending out of the inhaler 1 as a pull off portion. As shown in FIG. 1, the housing forms a disposable unit for a single dose. Please note, that the invention is not limited to the use of blister pockets as compartments for the powdered medicament.

An air inlet 27 is provided on the rear 25 of the inhaler, generally opposite the mouth piece 13. The thickness of the top plate 17 is reduced locally, so that during inhalation through the mouth piece 13, air may enter between the top plate 17 and the intermediate plate 18 to entrain powder from supply region 8 and carry it into the powder channel 7a. Please note, that other embodiments for creating an air inlet are also possible.

The flow of air entrains the powder and carries it through the wide channel 7a formed between the bottom 19 plate and intermediate plate 18 to the classifying chamber 2. In the embodiment shown in FIG. 1, the flow of air passes via aperture 11 in the intermediate plate 18 and trough the supply region 8 formed by the opened blister pocket. The air passes through aperture 11 into the opened blister for entrainment of the powder and the powder flow is guided over the downstream wall of the blister cup through a channel profiled at the bottom side of the centre plate. This channel with inclining and declining depth starts at approximately ½ the length of the blister pocket and ends over the declining part of the powder channel towards the classifier and has its maximal depth at 50% of its length.

An air flow without powder flows from the central inlet 27 at the rear 25 of the housing through a joint channel 7b to the supply channels 7 formed between the projections 20 and bottom plate 19 and the intermediate plate 18 to the chamber 2. In the shown embodiment the joint channel 7b runs parallel to the powder channel 7a which latter is situated opposite the joint channel when seen from the longitudinal axis MP of the inhaler.

Powder particles are thus introduced into the chamber 2 by entrainment with air entering tangentially into the chambers 2 through the powder supply channel 7a. Additional air is supplied to the chambers 2 through supply channels 7, which also enter tangentially into the chambers. This way, a circular air flow is created in the chamber 2 during inhalation and as a result of the relatively large diameter of the chamber 2 the circulation is sufficient for higher doses of medication. By distributing the relatively large number of supply channels 7 evenly about the circumference of the chamber, the circulation of the flow in the chambers 2 is further enhanced.

In addition, as a result of the seven line segments or sides 5a-5g the contact surface area between circulating particles and the wall is—compared to the prior art—reduced which attributes to a reduction of compaction of powder against the wall parts. A further reduction of compaction is obtained in that the collision angle, more detailed explained with regard to FIG. 2, is only approximately 45°. The high number of air channels results in an improved symmetry of the flow within the classifier chamber in which the smaller particles circulate at a certain distance from the polygonal sidewall. This prevents that they do collide with the sidewall, thereby preventing adhesion and compaction against this wall. Flow symmetry can be further influenced by lengthening the wall 20g' of the projection 20g forming one of the walls of the powder channel 7a. Due to the relatively wide powder channel 7a, which is at least twice as wide as the air flow channels 7 and preferably three times as wide, clogging of the powder channel 7a is strongly reduced.

Due to the polygonal shape of the chamber 2, the at least six sides 5, and the relatively large diameter of the chamber the powder particles break up correctly, i.e. they are correctly dispersed while retention is strongly reduced, so that the inhaler is suitable for strongly hygroscopic and compacting powders. Furthermore, finer particles are effectively entrained with the air flow exiting the chamber 2 axially through the air outlet 9 under the action of dominant drag forces.

Larger particles, including sweeper crystals used to clean deposited particles from the walls of the chamber 2, remain in the chamber 2 under the action of dominant centrifugal forces unless they break up. A further advantage of the inventive inhaler is that even in case the dry powder does not contain sweeper crystals the sides 5 of the chamber can remain clean.

The air flow exiting the chamber axially though the air outlet flows into the discharge channel leading to the mouth piece 13.

As the discharge channel 12 has a central axis MP that extends perpendicularly to the central axis 4 of the chamber 2, the discharge 12 channel connects transversely to the central axis of the air outlet 9 of the chamber 2, which coincides with the central axis 4 of the chamber 2, it is achieved that the flow from the air outlet 9 to the discharge channel changes direction from coaxial to the chamber axis to transverse to the chamber axis before exiting the mouthpiece 13. This way, the tangential component in the flow is decreased, so that mouth deposition is reduced without the need to provide a sheath flow. This increases the efficiency of the actual delivery of medicine to the lungs.

The powder in the dose compartment 23 may be the active ingredient or a formulation with the active ingredient being e.g. an unprocessed powder, a spherical pellet formulation, an adhesive mixture or a physical mixture, and/or a carrier excipient respectively a sweeper excipient, whereby the properties of the powder (formulation) may be adjusted to the specific properties of the classifier. A single dose of the active ingredient (with or without excipients) may be divided over a plurality of dose compartments pocket 23 for either simultaneous or subsequent inhalation. Each compartment may contain the same component or mixture, or may contain different components or mixtures. The compartments may be loaded from a metering apparatus in the housing, but are preferably pre-filled.

In FIGS. 2 and 3 another embodiment of a breath actuated dry powder inhaler 201 is shown, in which the polygonal sidewall has eleven straight line segments or sides 205*a*-205*k* (only the sides 205*a* and 205*k* are shown for convenience of drawing), which are formed by a surface of a respective projection 220. The projections 220*a*-220*b*, 220*b*-220*c*, 220*c*-220*d*, 220*d*-220*e*, 220*e*-220*f*; 220*f*-220*g*; 220*g*-220*h*; 220*h*-220*i*; 220*i*-220*j* and 220*j*-220*k* are spaced at the same distance from each other so as to form a plurality of air supply channels 207 (in the embodiment shown in FIGS. 2 and 3 ten) which have the same width and which are regularly disposed about the circumference of the chamber. The projections 220*a* and 220*k* are again spaced at a larger distance from each other forming a powder channel 207*a*. As a result of the eleven side sides 205*a*-205*k* the contact surface area between circulating particles and the wall is even further reduced which attributes to a reduction of compaction of powder against the wall parts. With regard to the embodiment of FIG. 1 a further reduction of compaction is also obtained in that the collision angle ca—i.e. the angle between the imaginary extension of the sides, is approximately 30°. This high number of air channels results in even better flow symmetry in the classifier chamber in which smaller particles circulate at a certain distance from the polygonal sidewall to prevent that they do collide with the sidewall thereby preventing that they contribute to adhesion and compaction. Again, the free edges of the projections are all positioned on an imaginary circle (indicated by broken lines). Please note that in order to avoid unnecessary repetition of the description of components reference is made to FIG. 1 in which the other analogous components of the inhaler are described. In FIG. 3 a locking clip 290 is additionally shown as the assembling element 214*a*.

The invention claimed is:

1. A breath actuated dry powder inhaler, said inhaler comprising:
a planar housing built up of a stack of planar elements, said planar housing having a longitudinal axis, said planar elements including a bottom plate, an intermediate plate and a top plate, said planar elements being parallel to each other, at least one planar element being provided with projections and an opening, that in the stack form a disc shaped air circulation chamber for de-agglomeration of entrained powdered medicament using energy of an inspiratory air stream, a plurality of air supply channels, an air supply region for a powder flow and a discharge channel of the inhaler, the chamber having a polygonal sidewall extending about a central axis between top and bottom walls of the chamber, the central axis extending perpendicular to the longitudinal axis of the planar housing and transversely to the bottom plate, a height of the chamber being smaller than a diameter of the chamber, the plurality of air supply channels being disposed about a circumference of the chamber, which channels extend from an air inlet and which channels enter the chamber tangentially to the polygonal sidewall of the chamber, the housing comprising a powder channel extending in a direction parallel to the longitudinal axis through a powder dose supply region of the inhaler to the chamber, which powder channel enters the chamber tangentially to the polygonal sidewall of the chamber, the chamber further comprising an air outlet axially extending from a discharge opening and connecting to a discharge channel that extends to a mouthpiece, wherein the discharge channel connects transversely to the air outlet of the chamber, characterized in that the inhaler comprises a single air circulation chamber and in that the polygonal sidewall comprises at least six straight sides, each straight side being spaced at a same first distance from an adjacent straight side forming the plurality of air supply channels, the air supply channels each having a same width defined by the first distance and being regularly disposed about the circumference of the chamber, the powder channel being defined by two straight sides which are spaced from each other at a second distance which is larger than the first distance, the second distance being a width of the powder channel.

2. The breath actuated dry powder inhaler according to claim 1, wherein the polygonal sidewall comprises eleven straight sides.

3. The breath actuated dry powder inhaler according to claim 1, wherein the second distance is at least twice the first distance.

4. The breath actuated dry powder inhaler according to claim 1, wherein the first distance is between 1 and 2 mm.

5. The breath actuated dry powder inhaler according to claim 1, wherein a straight side of the polygonal sidewall is formed by a side surface of each of the projections, each side surface having a free edge, the free edges of the side surfaces of the respective projections being rounded off and situated on a circle around the central axis.

6. The breath actuated dry powder inhaler according to claim 1, wherein the diameter of the single chamber is between 20 mm and 30 mm.

7. The breath actuated dry powder inhaler according to claim 3, wherein the second distance is three times the first distance.

8. The breath actuated dry powder inhaler according to claim 4, wherein the first distance is 1.5 mm.

9. The breath actuated dry powder inhaler according to claim 6, wherein the diameter of the single chamber is 25 mm.

* * * * *